(12) United States Patent
Gallagher et al.

(10) Patent No.: US 7,343,074 B1
(45) Date of Patent: Mar. 11, 2008

(54) OPTICAL WAVEGUIDE ENVIRONMENTAL SENSOR AND METHOD OF MANUFACTURE

(75) Inventors: Michael Thomas Gallagher, Corning, NY (US); Karl William Koch, III, Elmira, NY (US); Ellen Marie Kosik Williams, Painted Post, NY (US); James Andrew West, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 11/711,199

(22) Filed: Feb. 27, 2007

(51) Int. Cl.
*G02B 6/02* (2006.01)
(52) U.S. Cl. ......................... 385/125; 385/12; 385/129; 385/132; 250/227.11
(58) Field of Classification Search ................ 385/12, 385/125, 129–132; 250/227.11
See application file for complete search history.

(56) References Cited

U.S. PATENT DOCUMENTS

| | | | | |
|---|---|---|---|---|
| 6,151,155 | A * | 11/2000 | Durfee et al. | 359/332 |
| 6,496,634 | B1 | 12/2002 | Levenson | 385/125 |
| 2003/0065091 | A1 | 4/2003 | Brann et al. | 525/64 |
| 2004/0179796 | A1* | 9/2004 | Jakobsen et al. | 385/123 |
| 2005/0047741 | A1 | 3/2005 | Sfez | 385/129 |
| 2006/0088265 | A1 | 4/2006 | Akiyama et al. | 385/129 |
| 2006/0098927 | A1 | 5/2006 | Schmidt et al. | 385/129 |

OTHER PUBLICATIONS

"Resonant Optical Interactions with Molecules Confined in Photonic Band-Gap Fibers", Ghosh, et al; Physical Review Letters; Mar. 11, 2005; pp. 1-4.

"Polarization-selective etching in femtosecond laser-assisted microfluidic channel fabrication in fused silica"; Hnatovsky et al; Jul. 15, 2005; vol. 30, No. 14; Optics Letters; pp. 1867-1869.

"Ultrahigh Efficiency Laser Wavelength Conversion in a Gas-Filled Hollow Core Photonic Crystal Fiber by Pure Stimulated Rotational Raman Scattering in Molecular Hydrogen"; Benabid et al; vol. 93; No. 12; Physical Review Letters; Sep. 17, 2004.

"Microfluidic sensor based on integrated optical hollow waveguides"; Campopiano et al; Optics Letters; vol. 29, No. 16; Aug. 15, 2004; pp. 1894-1896.

"Microstructure fibres for optical sensing in gases and liquids"; Institute of Physics Publishing; Fini; pp. 1120-1128; published May 13, 2004.

(Continued)

*Primary Examiner*—Brian Healy
*Assistant Examiner*—Hung Lam
(74) *Attorney, Agent, or Firm*—Svetlana Z. Short

(57) ABSTRACT

An optical waveguide environmental sensor is provided that is capable of detecting a target gas or liquid in the ambient environment in an advantageously short period of time. The waveguide is preferably in the form of an optical fiber having a cladding that contains a photonic band gap structure which in turn envelopes a light conducting, hollow core portion. The cladding further includes at least one elongated side opening that preferably extends the entire length of the fiber and exposes said hollow core portion to the ambient environment, which provides broad and nearly immediate access of the core portion to gases and liquids in the ambient environment, thereby minimizing sensor response time. The ambient gases or liquids filling the hollow core portion and elongated opening function as a ridge and slab, respectively, of an optical ridge waveguide that effectively supports at least one bound optical mode.

43 Claims, 12 Drawing Sheets

OTHER PUBLICATIONS

"A review of IR transmitting, hollow waveguides"; Fiber and Integrated Optics, 19, 211-217 (2000); Harrington.

"Measurement of Gas Diffusion Coefficient Using Photonic Crystal Fiber"; IEEE Photonics Technology Letters; vol. 15, No. 10, Oct. 2003, Hoo et al.

"Photonic crystal fiber based evanescent-wave sensor for detection of biomolecules in aqueous solutions"; Jensen et al; Optics Letters, vol. 29, No. 17; Sep. 1, 2004; pp. 1974-1976.

"Semiconductor hollow optical waveguides formed by omni-directional reflectors"; Lo et al; Optics Express; Dec. 27, 2004; vol. 12, No. 26; p. 6589-6593.

"Water-Core Fresnel fiber"; Martelli et al; Optics Express; May 16, 2005; vol. 13, No. 10; pp. 3890-3895.

"Gas sensing using air-guiding photonic bandgap fibers"; Ritari et al; Optics Express; Aug. 23, 2004; vol. 12, No. 17; pp. 4080-4087.

"Optical Transmission Loss in Liquid-Core Hollow Fibers"; Stone; IEEE Journal of Quantum Electronics; Mar. 1972; p. 386-388.

"A long pathlength liquid-core waveguide sensor for real-time pCO2 measurements at sea"; Wang et al; Marine Chemistry 84 (2003) 73-84.

"Integrated ARROW waveguides with hollow cores"; Schmidt et al; Optics Express, Jun. 14, 2004; vol. 12, No. 12; pp. 2710-2715.

"Femtosecond laser-assisted three-dimensional microfabrication in silica"; 2001 Optical Society of America; Optics Letters; Mar. 1, 2001; vol. 26, No. 5; pp. 277-279.

"Stimulated Raman Scattering in Hydrogen-Filled Hollow-Core Photonic Crystal Fiber"; Benabid et al; Science; Oct. 11, 2002; vol. 298; pp. 399-402.

\* cited by examiner

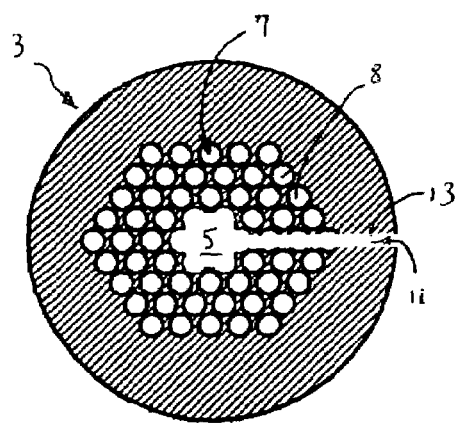
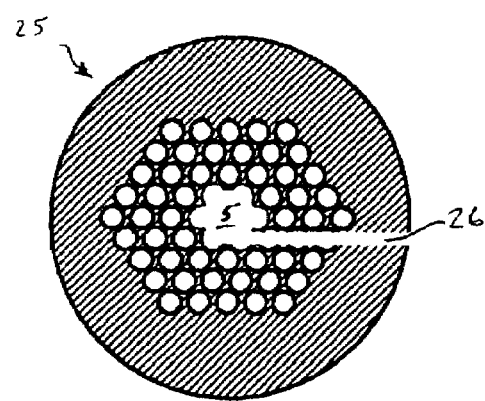
FIGURE 2A  FIGURE 2B
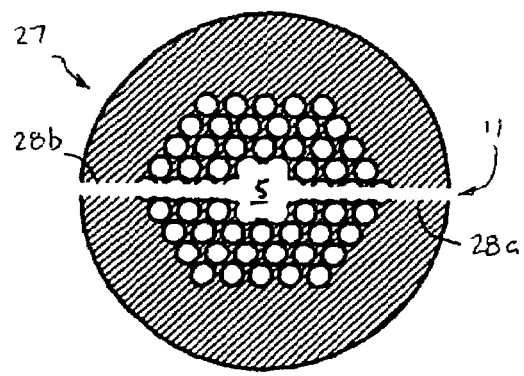
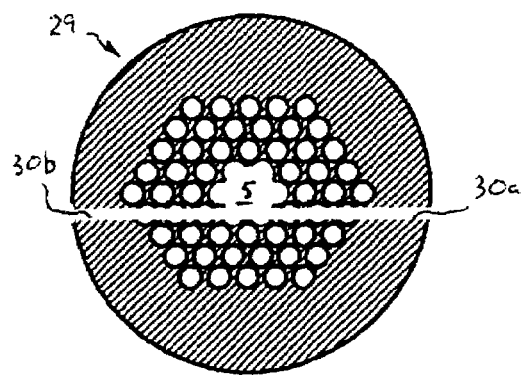
FIGURE 2C  FIGURE 2D
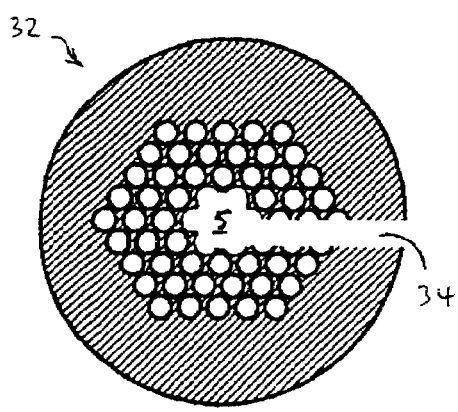
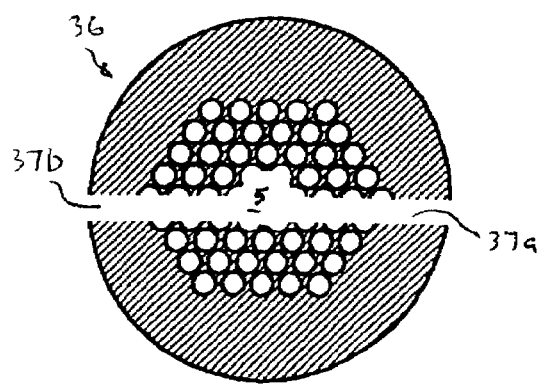
FIGURE 2E  FIGURE 2F

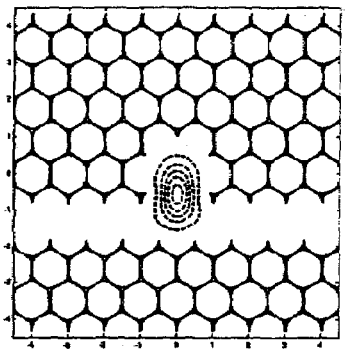 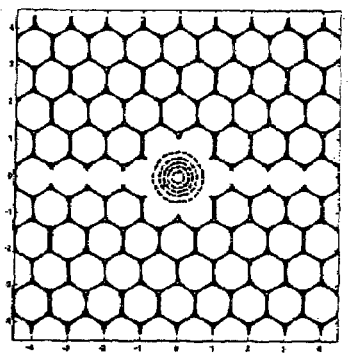 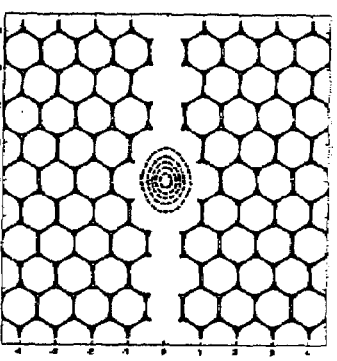
FIGURE 5A  FIGURE 5B  FIGURE 5C
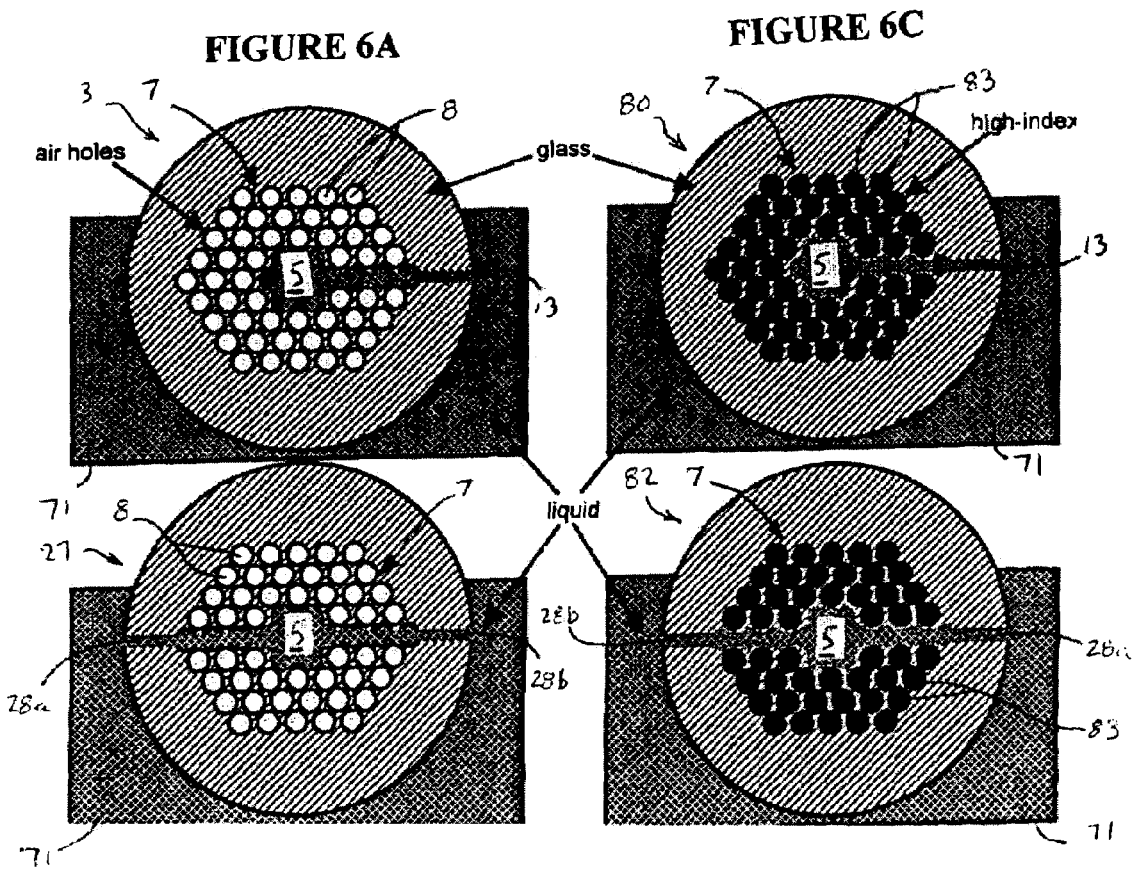
FIGURE 6A  FIGURE 6C
FIGURE 6B  FIGURE 6D

1000 mm bend 10 mm bend 5 mm bend

OPTICAL WAVEGUIDE ENVIRONMENTAL SENSOR AND METHOD OF MANUFACTURE

FIELD OF THE INVENTION

This invention generally relates to an optical waveguide environmental sensor and the method of manufacturing the same, and is specifically concerned with such a sensor in the form of a photonic band gap fiber having an elongated side opening that exposes its hollow core to the ambient environment.

BACKGROUND OF THE INVENTION

Environmental sensors in the form of optical fibers having a hollow core are known in the prior art. The hollow core of the fibers used for such sensors typically conducts light by way of a photonic band gap structure (PBG) surrounding the hollow core having a "forbidden frequency range" which corresponds to the wavelength of the light transmitted through the fiber, although hollow core fibers that conduct light via total internal reflection (TIR) for a specific range of wavelengths are also known. Such sensors may be used to sense the presence of a particular gas or liquid in the ambient environment, for example a threshold amount of carbon dioxide in the ambient air which may be indicative of a fire or other unsafe condition. In one prior art design, the hollow core of the optical fiber is exposed to the ambient atmosphere at one or both of the ends of the fiber to allow gases from the ambient atmosphere to continuously flow into a hollow core of the fiber. In operation, laser light having a wavelength which would be absorbed by the particular gas composition to be a detected is continuously conducted through the hollow core of the fiber. When such a gas is introduced into the open end of the fiber from the ambient atmosphere, it begins to flow through the hollow core, and the amplitude of the laser light transmitted through the core diminishes due to absorption of the light by the gas. In the case of the carbon dioxide example referred to earlier, the diminishment of the amplitude of the light below a certain threshold may be used to generate a signal that triggers a fire alarm circuit.

Such environmental sensors may be used to detect a broad variety of different gas compositions in the atmosphere, organic and inorganic particulates or vapor droplets, and even different liquid compositions when the fiber is immersed in a liquid. Hence such sensors have a broad applicability as detectors of not only combustion products or polluting or potentially toxic substances, but also as control or monitoring sensors in industrial manufacturing processes where the control of the composition of a particular gas or liquid is required.

Unfortunately, there are a number of shortcomings associated with such prior art optical fiber environmental sensors. As previously pointed out, access to the ambient environment is provided only at one or both of the ends of the fiber, where the relatively tiny diameter of the hollow portion is exposed to the outside atmosphere. Such restricted access to the hollow core of the sensor fiber results in a relatively long response time for such a sensor to detect a particular "target" gas or liquid. For example, for a known optical fiber sensor having a length of 21 cm, a response time of 2 minutes is required from the time that the target gas or liquid is first introduced into the hollow core of the fiber before the fiber sensor generates a signal indicating that the target gas or liquid is present. Such a long response time substantially limits the usefulness of such sensors in many applications, such as chemical manufacturing applications, where a 2 minute delay may result in the irretrievable ruin of a production run of an expensive composition.

Thus far, no satisfactory way to shorten the response time for such sensors has been found. Of course, the length of the optical fiber sensor could be shortened, but such shortening not only reduces the sensitivity of the sensor (as sensitivity is proportional to the total volume of the hollow core) but also makes it apt to generate false positives (as a single tendril of cigarette smoke curling around a 1 cm smoke detector may trigger it).

Another solution to shorten the response time might be to make the diameter of the fiber air core larger. Such a solution might be implemented by using capillary tubes with hollow cores having a diameter on the order of 1.0 mm that conduct light via grazing incidence scattering rather than by the use of TIR or a PBG. However, such capillary tube optical waveguides have high light losses of over 1 dB/m, which imposes practical limits on the length of such a sensor, and are also relatively stiff and inflexible, which prevents them from being installed in space-limited situations where a sharp bending or tight coiling of the sensor is desired. To reduce the losses associated with such a capillary tube design, the hollow interior of the tube might be coated with alternating layers of materials having sharply different indexes of refraction, thereby creating a Bragg reflector, or a single layer of a material having an index of refraction less than air. However, such coated capillary tubes would be substantially more expensive to manufacture than drawn optical fibers. Additionally, the losses would still be greater than 0.5 dB/m, and the problems associated with stiffness and inflexibility would remain. In addition, many optical sensing operations rely on nonlinear optical effects (Raman spectro-scopy, for example) for which the sensitivity is proportional to the intensity (power per area) of the optical signal. A larger optical core will cause the intensity of the light in the core to decrease by a factor proportional to the square of the diameter of the core thereby reducing the device sensitivity by the same factor.

Finally, it has been proposed to laser drill a plurality of circular side holes in the fiber to better expose the hollow core to the ambient atmosphere. While such a solution may shorten the response time of the fiber sensor, the resulting response time would still be unacceptably long due the fact that access to the hollow core is still quite limited. Additionally, there is a concern in the prior art that such radially-oriented side openings create "light leaks" that limit the number of side openings that can be fabricated in such a fiber before the resulting losses become unacceptably high.

Clearly, what is needed is an optical waveguide environmental sensor that maintains the low losses, flexibility and ease of manufacture associated with optical fibers, but which substantially reduces the response time associated with fiber-based environmental sensors that rely upon a relatively small number of end or side holes to expose the hollow core of the fiber to the ambient environment.

SUMMARY OF THE INVENTION

Generally speaking, the invention is an optical waveguide environmental sensor that overcomes the aforementioned shortcomings associated with prior art. To this end, the environmental sensor of the invention comprises a cladding having a hollow core portion that extends along or parallel to a longitudinal, center axis of the cladding and defines a light transmission path through the waveguide, and at least one elongated side opening in the cladding that extends parallel to the longitudinal center axis and directly exposes all or a substantial part of the side of the hollow core portion to the ambient environment, wherein the hollow core portion and the elongated opening support at least one bound optical mode. The optical waveguide is preferably an optical fiber that includes a photonic band gap structure which envelops the hollow core portion. The photonic band gap structure may assume the form of either a Bragg reflector that includes alternate layers of material having sharply different indexes of refraction, or a microstructured material having a periodic variation in an index of refraction. In operation, when a gas or liquid from the ambient environment fills the hollow core portion and the elongated opening in the cladding, the hollow core portion and elongated opening form a ridge and a slab, respectively, of an optical ridge waveguide sensor that binds an optical mode to the hollow core portion.

The elongated opening preferably runs most or all of the length of the waveguide in order to maximize exposure of the side of the hollow core portion to the ambient environment and to minimize the response time of detection, preferably to seconds or less. The optical waveguide may have a plurality of such elongated openings, each of which operates to expose a side of the hollow core portion to the ambient environment and to further reduce response time. To eliminate optical birefringence, the plurality of elongated openings may be symmetrically disposed around the cladding.

The elongated opening may take the form of a slot-like groove having parallel side walls. Such a slot-like opening may extend through only through one side of the cladding to the hollow core portion, or completely through the cladding thereby exposing two sides of the hollow core portion. Alternatively, the elongated opening may be formed by the removal of a wedge-shaped section of cladding such that the side walls of the opening are disposed at an angle to one another when the waveguide is viewed in cross section. Finally, the elongated opening may also be formed by the removal of a flat-sided section of cladding such that the side walls of the elongated opening are co-planar, thus giving the optical fiber sensor a "D"shaped profile when viewed in cross section. When the elongated opening is formed in this last-described manner, the optical fiber is preferably bent around a radius in a spiral configuration with the flat side of the "D" shaped profile on the inside of the bend in order to reduce light losses in the resulting fiber, as the optical mode conducted through the resulting ridge waveguide is more weakly bound by such an open configuration of the hollow core portion.

The optical fiber sensor of the invention may also have multiple hollow cores which are preferably optically coupled to one another. For example, in such embodiment, one or all of the hollow core portions may be exposed to the ambient environment by one or more elongated openings. For example, in such a sensor one hole may be isolated from the environment to act as a reference optical path, while the other core or cores may be exposed to the environment, thereby producing an interferometric sensor in which light in the reference optical path will interfere with light in the sensing optical path yielding a signal that is related to the concentration of the target gas or liquid species. Such a differential or interferometric sensor according to some embodiments of the present invention can remove the effect of other environmental changes such as temperature and pressure.

Finally, the invention also encompasses a method of fabricating an optical waveguide environmental sensor that comprises the steps of forming an elongated optical waveguide from a light conducting material that contains a hollow core portion surrounded by photonic band gap structure, and forming an elongated opening in a side of said waveguide that is parallel to a longitudinal axis of said waveguide that exposes said hollow core portion to the ambient environment. Preferably, the step of forming said elongated optical waveguide is implemented by the drawing of an air-core photonic band-gap fiber from a light conducting material, while the step of forming the elongated opening is implemented by chemically etching said opening in a side wall of said fiber. When such chemical etching is used to form the elongated opening, a glass composition may be provided in a side of said optical fiber that has a higher etch rate to facilitate the step of chemically etching said opening in a side wall of said fiber. Alternatively, the elongated opening may be formed by laser machining (for example, drilling) said opening in a side wall of said optical fiber. The term "laser machining" as used herein, includes but is not limited to various forms of laser assisted material removal, material redistribution and material modification.

DESCRIPTION OF THE DRAWINGS

FIGS. 2A-2G are side, cross-sectional views of different embodiments of the fiber sensor wherein the hollow core is centered in the lattice forming the microstructure, and the elongated side opening is in the form of a radial, semi-chordal, diametral, and chordal slot along the x-axis of the lattice;

FIGS. 5A-5C illustrate optical intensity contours at 10%, 30%, 50%, 70% and 90% of the calculated fundamental optical modes for the embodiments illustrated in FIG. 2D, for a photonic band gap fiber with a narrow horizontal slot, and for the embodiment illustrated in FIG. 3C, generally illustrating the amount of mode confinement offered by different embodiments of the invention;

FIGS. 6A-6D are side, cross-sectional views of different embodiments of the fiber sensor used to sense an ambient liquid, wherein the elongated side opening takes the form of a radial or a diametral slot, and the lattice is formed from either a pattern of air holes or a high index glass, liquid or plastic;

DETAILED DESCRIPTION OF THE PREFERRED EMBODIMENTS

Figure 1:
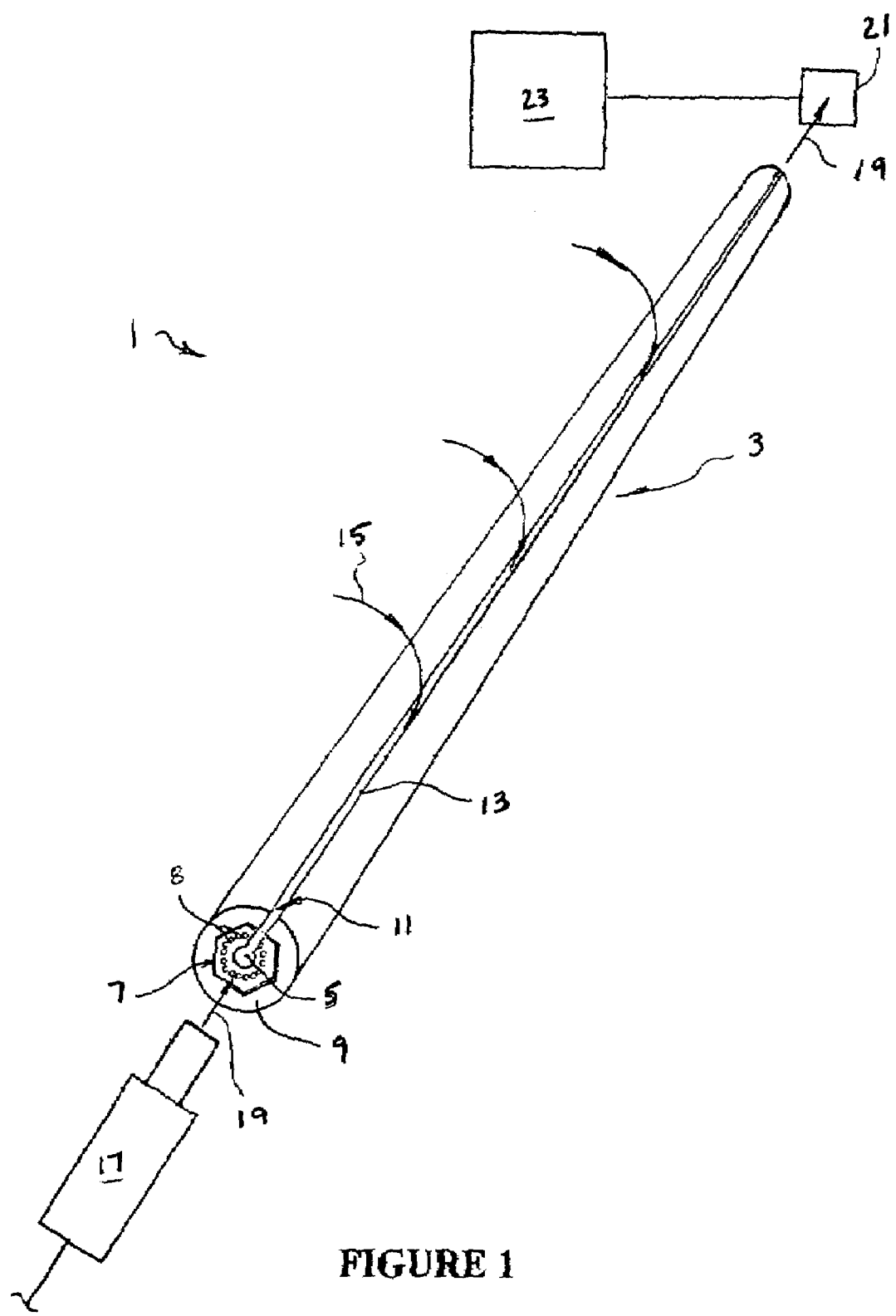
FIG. 1 is a perspective view of the optical fiber environmental sensor of the invention in operation in an alarm system.

With reference now to FIG. 1, wherein like numerals designate like components throughout all the several figures, the optical waveguide sensor 1 of the invention preferably comprises a photonic band gap fiber 3 having a lattice-type microstructure 7 hereinafter referred to as cladding 7. The cladding 7 includes a pattern of different light conducting materials having different indexes of refraction, such as a pattern of air holes 8 (shown in FIGS. 2A-4F) in the silica present in the center of the fiber 3. Alternatively, the cladding 7 may be formed from an alternating pattern of two different solid light conducting materials, such as two different types of glasses, or a glass and a plastic material. Finally, the cladding 7 may be formed from alternating layers of such materials, so long as the differences in the index of refraction between the two materials effectively creates a "forbidden zone" that confines a least one optical mode within the hollow core 5. The cladding 7 is in turn surrounded by a jacket 9. The jacket 9 includes an elongated side opening 11, which, in this example, is a slot 13 that extends substantially the length of the fiber 3. The slot 13 is radially oriented with respect to the circular cross-section of the fiber 3 and exposes a hollow core 5 to the ambient environment, which in this example is the ambient atmosphere. Together the core 5 and slot 13 form a waveguide that guides optical modes that are supported by the joint optical structure. The core 5 is a local enlargement of the slot 13 such that at least one optical mode is supported with a significant fraction of its energy localized to the enlarged region. The mode would have greater than 50%, most preferably more than 75% of its energy in the enlarged region. In operation, ambient gas 15 is allowed to continuously flow through the slot 13 and into the hollow core 5 of the fiber. A source 17 of light (for example, laser light) is optically coupled to one end of the fiber 3 and projects a beam 19 through the hollow core 5. The light source 17 may include a quasi-monochromatic laser source, multiple laser sources (co-propagating or counter-propagating), a broadband light source (such as a tungsten halogen lamp, glow bar, spectral lamp, etc), light-emitting diodes or any other source that is used in sensing applications. The hollow core 5 and the radially oriented slot 13 jointly support at least one optical mode, and more specifically function as the ridge and slab, respectively, of an optical ridge waveguide that supports the propagation of at least one optical mode with more than half of its optical power confined to the region defined by the hollow core 5 and the portion of the radially oriented slot 13 that is directly adjacent to the hollow core 5. The slab in this case does not end at the outer surface of the jacket 9 with the end of the elongated side opening 11, but continues into the ambient atmosphere, thereby forming a "semi-infinite" slab. The center frequency of the beam 19 of light (for example, laser light) is selected so as to be absorbable or modified by a target gas, liquid or particulate substance within the ambient air 15. For example, if the optical waveguide sensor is being used as a fire detector, the central frequency of the beam 19 of light may be selected so as to be absorbed by carbon dioxide. A light sensor 21, which may be a phototransistor, receives the beam 19 of laser light exiting the opposite end of the photonic band gap fiber 3, and generates an electric signal having an amplitude that is dependent upon the amplitude of the beam 19 exiting the end of the photonic band gap fiber 3. The light sensor 21 is in turn connected to a digital processor circuit 23, which continuously monitors the amplitude of the electrical signal generated by the light sensor 21. The processor circuit 23 is programmed such that when the amplitude of the signal received by the light sensor 21 falls below a selected threshold, an alarm circuit (not shown) is triggered.

Alternatively, more elaborate detection methods may be utilized to enhance sensitivity, selectivity, or to add functionality to the sensor. Such schemes may include but are not limited to differential detection (including multiple wavelengths or multiple optical paths), nonlinear spectroscopy (including Raman, coherent anti-Stokes Raman scattering, Brillouin scattering) interferometric detection, polarization-based detection, modal detection, distributed sensing (using nonlinear effects, scattering or optical time domain reflectometry), multi-wavelength detection or a combination of these.

Because the elongated side opening 11 in the photonic band gap fiber 3 provides near immediate access of ambient gases 15 to the hollow core 5 of the fiber 3, the response time of the optical waveguide sensor 1 is nearly immediate. Also, because of the relatively low losses associated with the optical ridge waveguide formed by the hollow core 5 and slot 13, the fiber 3 may be on the order of 10 meters or more long, which in turn results in a high sensitivity and allows the fiber 3 to broadly sample the ambient gases present in a particular area, thereby reducing the chances of false positives and thereby enhancing the over all reliability of the sensor 1.

FIGS. 2A-2G are side, cross-sectional views of different embodiments of the photonic band gap fiber sensor 3 of the invention, wherein the hollow core 5 is centered in the cladding 7 forming the microstructure, and the elongated side opening 11 is in the form of a radial, semichordal, diametral, and chordal slot along the x-axis of the lattice.

Figure 2G:
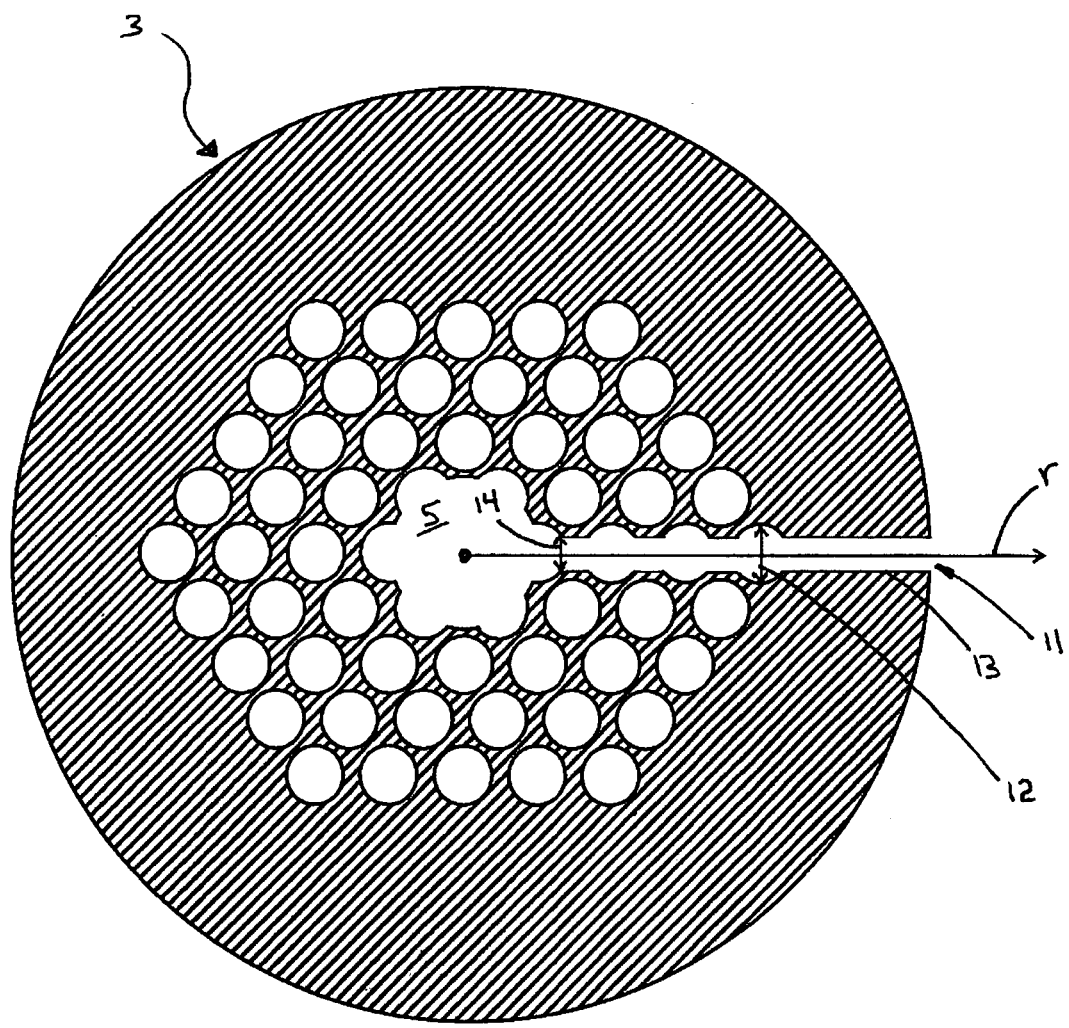

In FIG. 2G, the photonic band gap fiber 3 has an axis along its length and has a transverse cross-section perpendicular to this axis. The slot 13 has a first axis co-linear to the fiber axis and has a second axis, or transverse axis, that lies perpendicular to the first, extending from the core 5 to the elongated side opening 11. In the presence of a lattice, the slot 13 may have a varying width 12 w(r) perpendicular its radial dimension r. Such is the case in FIGS. 2A-2G because of the air holes 8 in the lattice. The width 12 of the slot is given by the minimum transverse width as measured perpendicular to the radial dimension referred to as the transverse axis. The location of the local width minima may be determined by computing a derivative of the slot width as a function of radial dimension such that dw(r)/dr=0 and the second derivative of the width with respect to r is positive. The core 5 (whose centroid is considered r=0) is given by the void in the periodic lattice that would exist in the absence of the slot 13. Because the core 5 and the slot 13 overlap at least partially, we define the core 5 to extend to include the overlap region to where the slot 13 has its first width minima 14, (as counted from r=0). In the case of multiple slots such as slot 28a and slot 28b in FIG. 2C, the core 5 extends to the first width minima along each slot. The hollow core 5 will in general have an irregular shape that may be characterized by a minimum transverse dimension D, a centroid location, an enclosed transverse area A and a perimeter p.

In the fiber sensor 3 illustrated in FIG. 2A, the cladding 7 is formed by a lattice of air holes 8. The lattice structure and materials are chosen such that cladding 7 has a photonic band gap over the targeted wavelength range. The scale of the structure is given a pitch $\Lambda$ that is defined as the spacing between unit cells of the periodic structure. In FIG. 2A that pitch would be given by the spacing between the centers of adjacent air holes. The wavelength range of the photonic band gap can be shifted by changing the pitch $\Lambda$, the refractive index n, the type of lattice, and the design of the unit cell of the lattice (including shape). The fiber sensor 3 can be designed for operation across the optical spectrum from the ultraviolet (100-400 nanometers) to the far infrared (20 microns). Although a single glass will not cover such a broad wavelength range without absorption, there are glasses with low optical absorptions in each portion of the spectrum. Examples of these glasses are fused silica, silicates, borosilicates, phosphates, germanates, chalcogenides, ionic glasses (such as halides, nitrates, sulfates and carbonates), and glass ceramics. Additionally optical polymers including acrylates such as PMMA and perfluorinated polymers provide sufficient optical transparency to be used in the embodiments of the invention.

The wavelength of operation is related to the pitch $\Delta$ of the lattice structure. For a lattice of air holes in silica the band gap is centered at a wavelength given by $\lambda = \Lambda$ for small air filling fraction (ratio of void volume to solid volume) to k=3.5$\Lambda$ for large air-filling fraction. As an example, for devices operating in the near infrared (800-2000 nanometers), the lattice pitch can be designed in the range from $\Lambda$=800-7000 nanometers. The core 5 would typically have a dimension D between D=0.7$\Lambda$ and 50$\Lambda$ and the slot 13 would have a minimum width greater than 0.5$\Lambda$. The structure would include multiple rows of holes spaced with pitch $\Lambda$ and would have an exterior jacket 9 to provide strength. The total diameter of the final fiber or waveguide would be between 50 microns and 500 microns.

Figure 10:
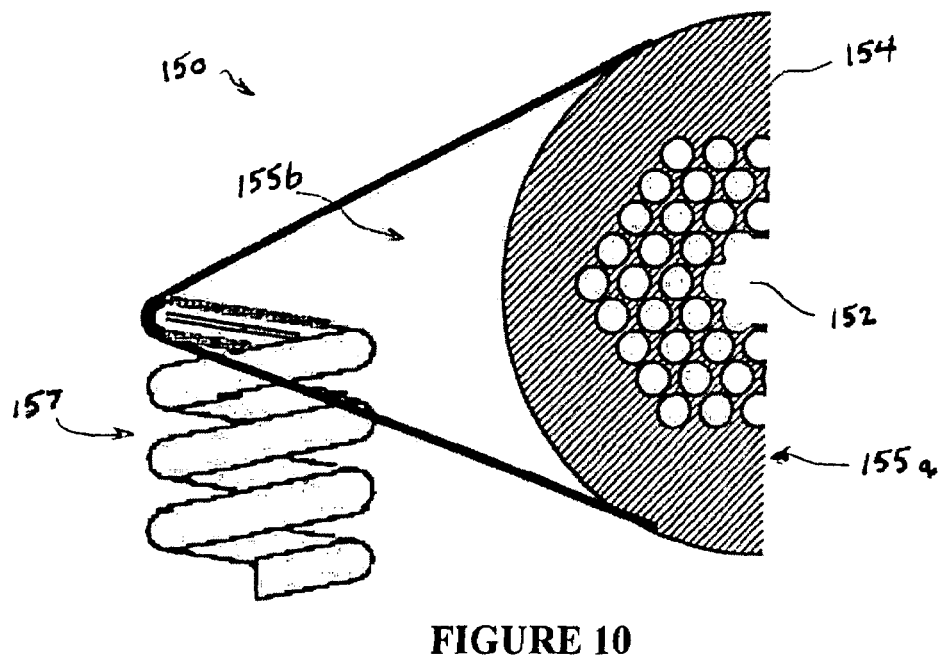
FIG. 10 is a schematic cross-sectional view of an embodiment of the fiber sensor that is similar to the ones illustrated in FIGS. 9A-9C, the difference being that the fiber has only a single, centrally disposed air core, wherein the fiber is coiled such that its open side forms the inner diameter of the coil in order to better confine an optical mode within the core.

In the fiber sensor 3 illustrated in FIG. 2A, the slot 13 is a single-sided slot having parallel, opposing side walls. Preferably, the slot 13 extends the length of the fiber sensor 3 in order to maximize exposure of the hollow core 5 to the ambient atmosphere. Slot 13 is radially oriented with respect to the circular cross-section of the fiber sensor 3. Such a single-sided slot 13 would have the advantage of relatively low losses for a beam of laser light transmitted through the hollow core 5 having a wavelength within the "forbidden zone" of the cladding 7, while the radial orientation of the slot 13 minimizes fluid flow resistance of outside gasses or liquids into the hollow core 5. Any losses could be further reduced by coiling the fiber sensor such that the slot 13 faced the inner diameter of the resulting coil or spiral for all the reasons given with respect to the FIG. 10 embodiment of the invention discussed hereinafter. In the fiber sensor 25 illustrated in FIG. 2B, a single-side slot 26 is also used. However, slot 26 is offset from the center of the hollow core 5 in a semichordal orientation that intersects with the bottom of the hollow core 5 as shown in order to minimize losses that may result from an overlap between "core" and "slot" modes of conducted light.

In the fiber sensors 27 and 29 illustrated in FIGS. 2C and 2D, double-sided diametral slots 28a, b and 30a, b are used. Such double sided slots 28a, b and 30a, b have the advantage of reduced fluid flow resistance as compared to the single-sided slots 11 and 26 discussed with respect to FIGS. 2A and 2B, which in turn increases sensitivity and reduces response time. However, these advantages are accompanied by somewhat larger losses in the light conducted through the fiber sensors 27 and 29. Also, the double-sided slots 28a, b and 30a, b cannot extend the full length of the fiber sensor 3, as it is necessary to periodically discontinue the slots so that the two halves of the fiber sensors 27 and 29 stay connected to one another via periodic webs of jacket 9. The center orientation of the diametral slot 28a, b of the fiber sensor 27 maximizes fluid flow through the hollow core 5, while the offset orientation of the chordal slot 30a, 30b of the fiber sensor 29 provides the same advantages in reducing overlapping modes as was discussed with the fiber sensor 25 of FIG. 2B with some reduction in fluid flow.

The fiber sensors 32 and 36 illustrated in FIGS. 2E and 2F have the same slot orientations as described with respect to FIGS. 2B and 2D, but with wider slots 34 and 37a, b, respectively, in order to improve fluid flow, but at a likely price of increased attenuation in optical signals transmitted therethrough.

Figure 3A:
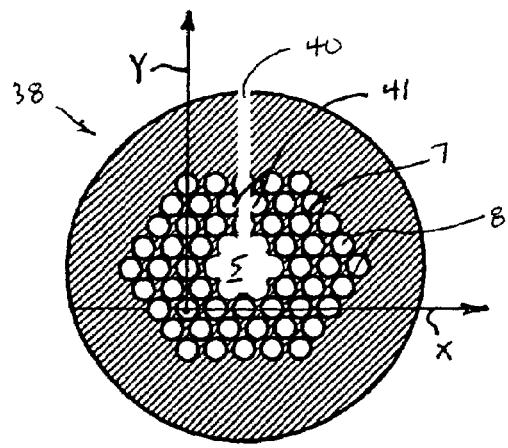
FIGS. 3A-3F are side, cross-sectional views of different embodiments of the fiber sensor wherein the hollow core is centered in the lattice forming the microstructure, and the elongated side opening is in the form of a radial, semi-chordal, diametral, and chordal slot along the y-axis of the lattice.
Figure 3B:
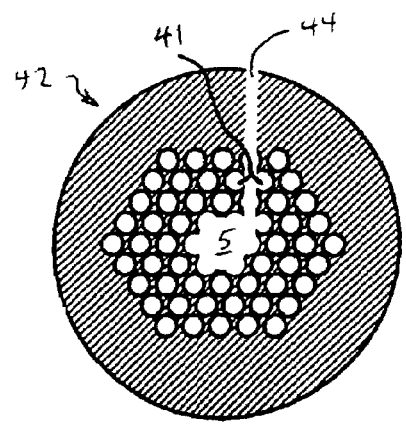

FIGS. 3A-F illustrate six additional embodiments 38, 42, 45, 48, 52 and 55 of the fiber sensor of the invention that are the same in structure as described with respect to the embodiments 3, 25, 27, 29 32 and 36 of FIGS. 2A-F, the only exception being that the slots 40, 44, 47a, b, 50a, b, 53 and 57a, b of these embodiments extend along the y-axis of the lattice of cladding 7. The orientation of the slot relative to the lattice of cladding 7 can affect the amount of optical signal attenuation in the embodiments of FIGS. 3A-D. With reference to FIG. 3A, note how the holes of the cladding 7 are arranged in rows that are parallel to the horizontal axis x, but which are staggered with respect to the vertical axis y. Hence, when the slot 40 of the fiber sensor 3 is cut along the vertical axis y, small optical cavities 41 are formed where the slot 40 intersects the opposing edges of two adjacent holes 8. The presence of these cavities 41 will change the slot modes in such a way that the overlap between core modes and slot modes will be decreased. This will lead to lower attenuation because of reduced coupling between the conducted modes of light due to structural perturbations along the fiber sensor 3. This same principle applies to the embodiments of FIGS. 3B-D, but not to the embodiments of FIGS. 3E-F, as the broader width of the slots 53 and 57a, b effectively opens the cavities 54 to the point where they no longer function to trap and more strongly bind the slot modes. However, the vertical orientation of the slots 53 and 57a, b will affect the optical attenuation in other ways.

Figure 3C:
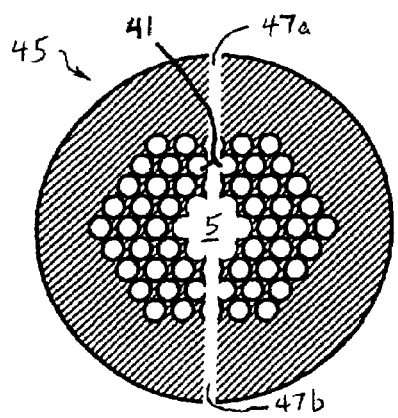
Figure 3D:
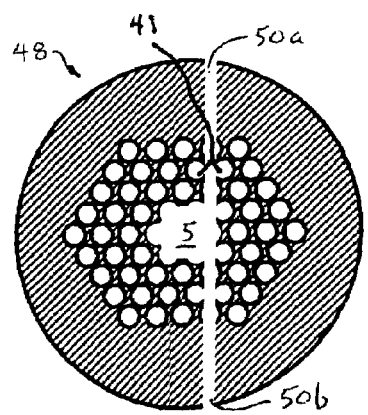
Figure 3E:
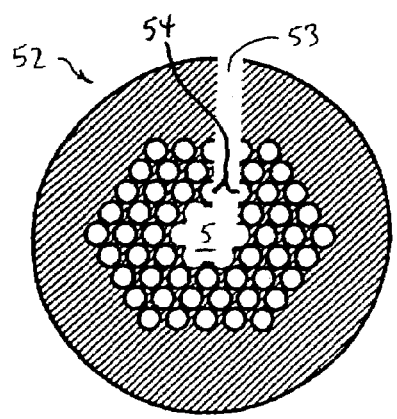
Figure 3F:
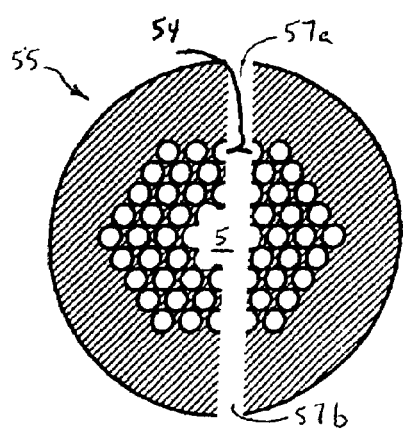
Figure 4A:
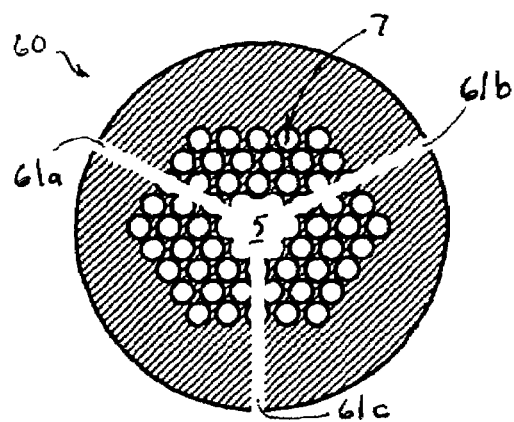
FIGS. 4A-4C are side, cross-sectional views of different embodiments of the fiber sensor wherein the hollow core is centered in the lattice forming the microstructure, and the elongated side opening is in the form of three radial slots uniformly disposed 120 degrees from one another and symmetrically positioned with respect to the core to eliminate birefringence.
Figure 4B:
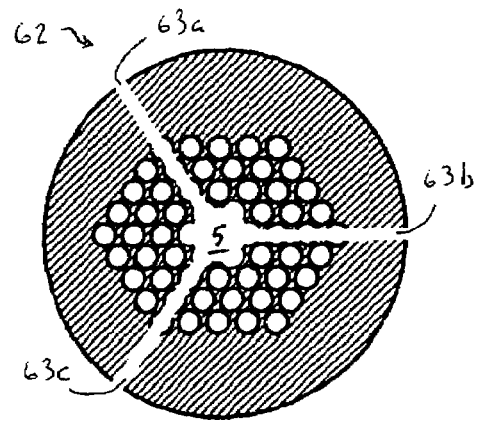
Figure 4C:
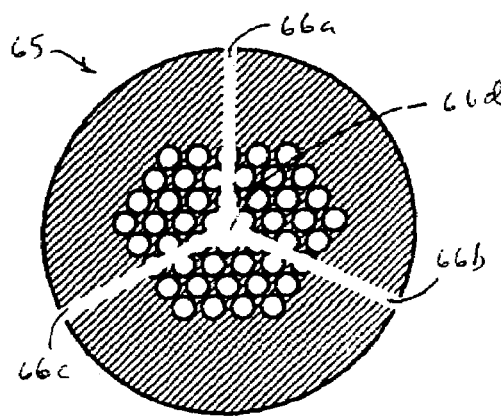
Figure 4D:
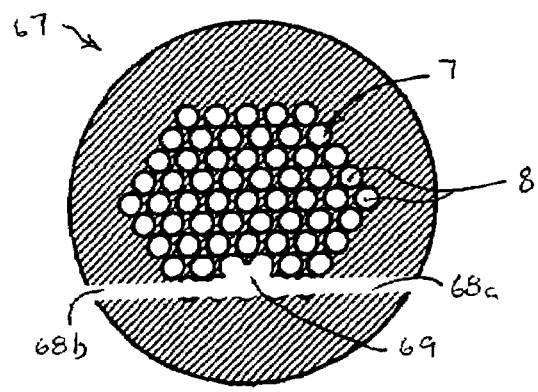
FIGS. 4D and 4E are side, cross-sectional views of different embodiments of the fiber sensor wherein the hollow core is hexagonal and triangular, respectively, and is not centered in the lattice forming the microstructure, and wherein elongated side opening is in the form of a chordal slot.
Figure 4E:
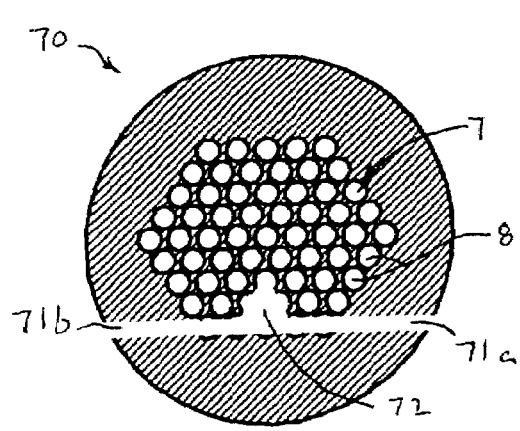
Figure 4F:
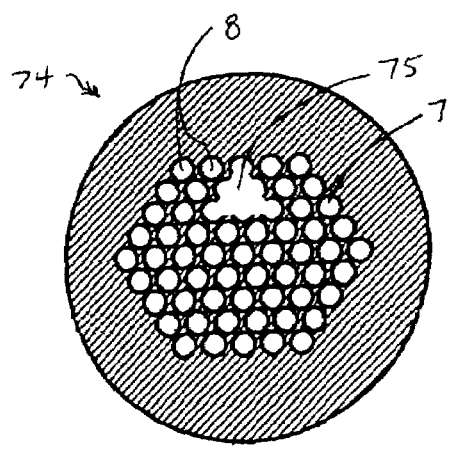
FIG. 4F is a side, cross-sectional view of a precursor fiber having an off-center hollow core that facilitates laser-machining or chemical etching into the fiber sensor of the invention.

FIGS. 4A-C illustrate embodiments 60, 62, and 65 of the fiber sensor that are isotropic, in contrast to the previously discussed embodiments which are all birefringent. The birefringent property of the previously discussed embodiments is the result of the less than three-fold symmetry in the structure. A consequence of this birefringence is that fundamental modes with different polarizations of the electric field will have different propagation constants and thus travel down the waveguide with different phase velocities, having the effect of splitting the incoming beam of light into two orthogonally polarized beams whose relative strengths is dependent upon the polarization of the incoming beam relative to the fiber structure. Birefringence can interfere with certain optical detection techniques that depend upon controlled polarization. Consequently, fiber sensors free of such birefringence are preferred for such applications. Birefringence is eliminated in the embodiments of FIGS. 4A-C by the provision of three slots 61a-c, 63a-c and 66a-c uniformly disposed 120 degrees from one another and symmetrically oriented with respect to both the center of the hollow cores 5 and 66d and the hexagonal profile of the cladding 7. Such designs produce the greater than two-fold rotational symmetry required to avoid birefringence. In contrast to the embodiments illustrated in FIGS. 2A through 4B, which are multimode fiber sensors, the embodiment 4C is a single mode fiber sensor by virtue of the relatively smaller cross-section of its hollow core 66d. While the inventors anticipate that most applications of the invention will call for a multimode transmission capability, the embodiment of FIG. 4C illustrates how the invention made be adapted for single mode transmission should the need arise. A device is considered to be single mode if there is only a single light mode (with one or two possible polarization states) with significant energy in the ridge portion of the waveguide. Additional modes may exist in the slab but they are not relevant because of their small overlap with the ridge region. FIGS. 4D and 4E illustrate embodiments 67, 70 of the invention where the hollow core 69, 72 is positioned to the side of the cladding 7 in order to facilitate the machining of the double-sided slots 68a, 68b and 71a, 71b. Such positioning of the cores 69, 72 relative to the cladding 7 reduces the number of holes 8 penetrated by either the chemical etching or laser machining used to form the slots 68a, 68b and 71a, 71b. In embodiments of the invention where the hollow core 5 is located in the center of the cladding 7, it is more difficult to precisely focus a laser beam since the holes 8 surrounding the hollow core 5 scatter the beam. Consequently, despite any losses which may be caused by the lack of a "forbidden zone" at the core/cladding interface due to the lack of lattice holes 8 in this area, it is anticipated that any such losses would be more than compensated for by reduced scattering from the smaller number of lattice holes 8 surrounding the hollow core 69, 72. Finally, FIG. 4F illustrates a precursor 74 to an embodiment of the invention where the hollow core 75 is located to the side of the cladding 7 to facilitate manufacture.

FIGS. 5A-5C are computer simulations of the shape of the fundamental optical mode for a fiber sensor having the slot configuration of FIG. 2D, for a photonic band gap fiber with a narrow horizontal slot, and for a fiber sensor having the slot configuration of FIG. 3C. Each of these Figures illustrates its respective mode by way of optical intensity contours circumscribing 10%, 30%, 50%, 70% and 90% of the peak intensity of the transmitted mode. While these simulations indicate the presence of some losses due to the presence of a slot, they more generally indicate the effectiveness of the ridge type waveguide formed by the hollow core and the slot in supporting an optical mode even though the cladding 7 does not completely surrounds the hollow core 5.

FIGS. 6A-6D illustrate embodiments of the invention 3, 27, 80 and 82 which may be used in a liquid environment 71. The specific structure of embodiments 3 and 27 has already been discussed. However, in a liquid environment, these embodiments 3, 27 would not conduct light through the aforementioned "forbidden zone" phenomenon since the cladding 7 constitutes a pattern of low index voids, which may be air holes 8, in a solid matrix. Instead, the fiber sensor embodiments 3, 27 would conduct light through the hollow core 5 via total internal reflection in much the same way a conventional optical fibers conduct light. More precisely, the guidance mechanism is that of modified total internal reflection found in solid-core photonic crystal fibers well known in the art. By contrast, the claddings 7 of the embodiments 80 and 82 are formed from a pattern of high-index voids 83 (which may be formed from a high-index glass, liquid or plastic) that would effectively create a "forbidden zone" that in turn would allow the fiber sensors 80 and 82 to conduct light as photonic band gap fibers. Again, the fiber sensors 6B and 6D would have better response times and sensitivity relative to the fiber sensors 6A and 6BC due to the provision of double-sided slots 28a, 28b vs. single slots 13. In this application, by low index, we mean that the effective index of the lowest energy mode of the cladding structure (holes plus matrix) is lower than the index of the material in the core region. Similarly, high is defined as the effective index of the lowest energy mode of the cladding structure (holes plus matrix) is higher than the index of the material in the core region. Whether the core refractive index is higher or lower than the effective index of the lowest energy mode of the cladding, structure can change as the wavelength of the optical field is changed.

Figure 7A:
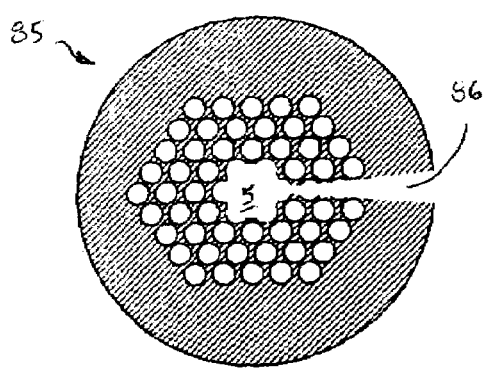
FIG. 7A is a side, cross-sectional view of an embodiment of the fiber sensor that is similar in structure to the embodiment illustrated in FIG. 2A, but wherein the elongated side opening takes the form of a radial, wedge-shaped slot.
Figure 7B:
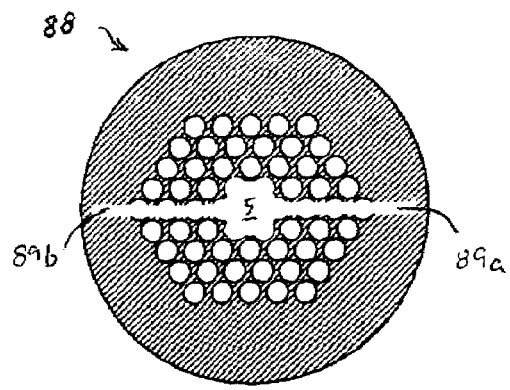
FIGS. 7B-7F are side, cross-sectional views of different precursor fiber designs having features such as internal void spaces, easily etched glasses and thin-sided cladding walls which facilitate the conversion of these precursor fibers into the fiber sensor of the invention.
Figure 7C:
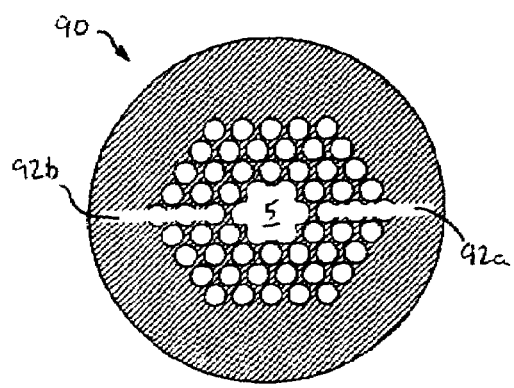
Figure 7D:
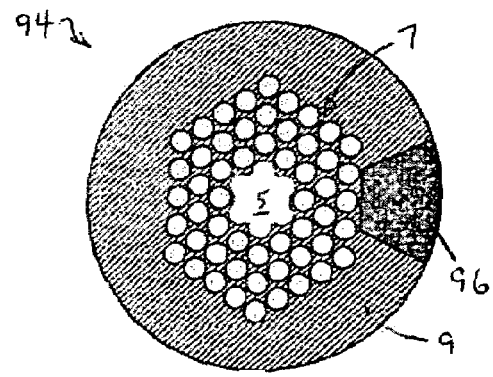
Figure 7E:
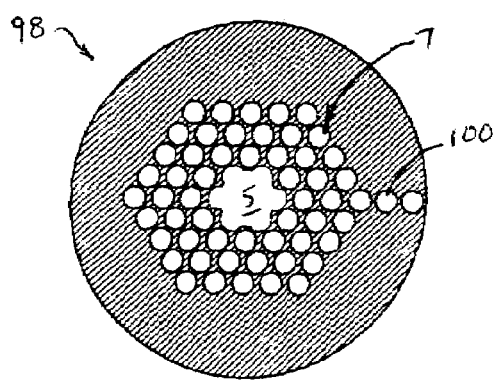
Figure 7F:
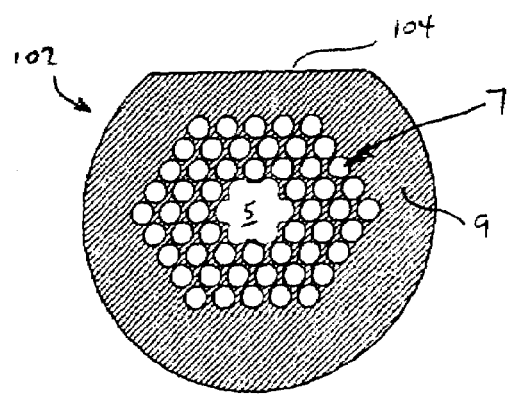

FIGS. 7A and 7B illustrate additional embodiments 85, 88 of the invention. The FIG. 7A embodiment 85 has a single sided slot 86 that is wedge-shaped as a result of being formed from a focused laser beam. The non-parallel sidewalls of the slot 86 would not significantly affect the optical performance of the resulting fiber sensor. The embodiment 88 of FIG. 7B can be either a precursor to a fiber sensor of the invention, or an alternative embodiment of the invention. This embodiment 88 includes a double-sided internal slot 89a, 89b that does not penetrate completely through the sides of the fiber sensor. Such internal slots 89a, 89b may be made in the preform stage and will remain in the fiber during the drawing process if the pressure of the air within the slots 89a, 89b is maintained at a certain level. When used as a precursor, the embodiment 88 can be laser machined a short distance between the outer radial ends of the slots 89a, 89b to the sides of the fiber to open the slots 89a, 89b up to the outside environment. When used as an alternative embodiment of the invention, the ends of the fiber may be opened to allow ambient gases to flow into the slots 89a, 89b and from there into the hollow core 5.

FIGS. 7C-7F illustrate four different precursors to the fiber sensors of the invention. In the precursor 90 shown in FIG. 7C, the double-sided slots 92a, 92b penetrate neither the hollow core 5 nor the side walls of the fiber. However, such a precursor may be easily converted into the fiber sensor of the invention by laser machining or etching the thin webs of glass separating the hollow core 5 from the slots 92a, 92b and the slots 92a, 92b from the side walls of the fiber. In the FIG. 7D embodiment 94, a section 96 of the side wall of the fiber is provided with a glass composition that is more easily etched or laser machined than the glass forming the balance of the cladding. Such a design is easily manufactured at the preform level of fiber fabrication. The section 96 extends to the edge of the cladding 7 as shown. While the core 5 is shown as being centrally located in the cladding 7, this embodiment could be modified so that the hollow core 5 was positioned on the side of the lattice adjacent to the glass section 96 to minimize the amount of etching or machining needed to expose the core 5 to the ambient environment. The FIG. 7E embodiment 98 includes a radially-extending row 100 of holes from the cladding 7 to facilitate the laser machining or etching of a slot from the side wall of the fiber to the hollow core 5. Finally, in the FIG. 7F embodiment 102, a section 104 of the side wall of the jacket 9 has been removed to again facilitate either the laser machining or the etching of a slot from the side wall of the fiber to the hollow core 5.

Figure 8A:
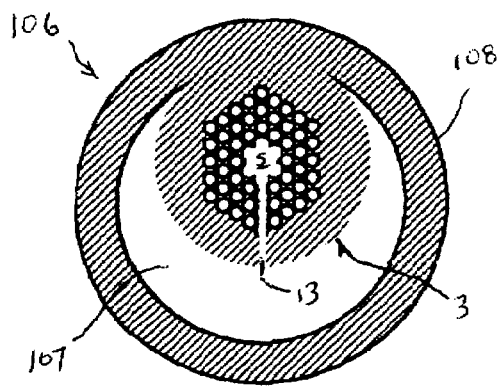
FIGS. 8A and 8B illustrate two different embodiments of the fiber sensor and its preform wherein the fiber sensor is enveloped in an overcladding to facilitate manufacture.
Figure 8B:
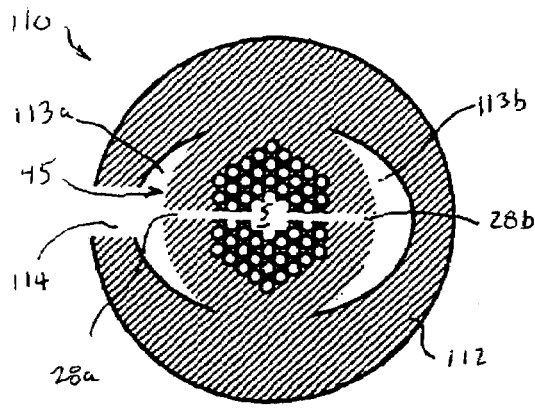
Figure 8C:
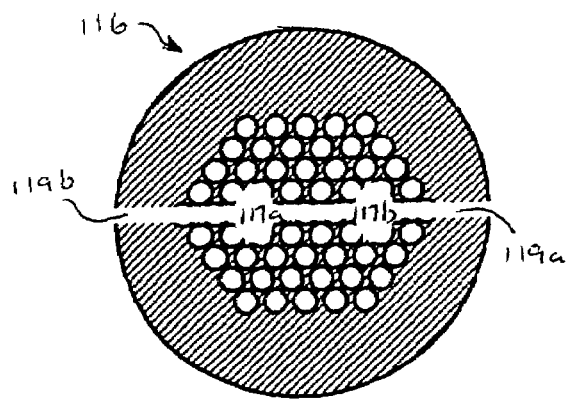
FIGS. 8C-8F are side, cross-sectional views of different embodiments of the fiber sensor having two hollow cores within the lattice, wherein one or more of these hollow cores is exposed to the ambient environment by way of either a diametral or radial slot.
Figure 8D:
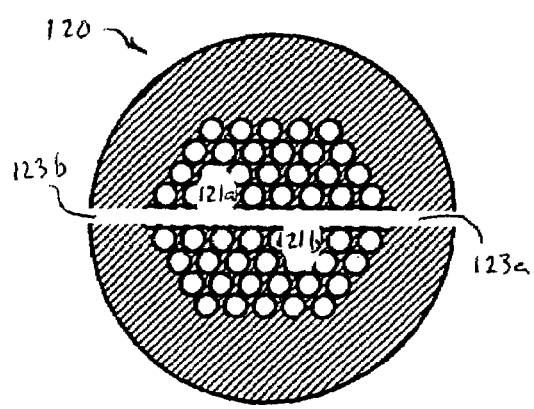
Figure 8E:
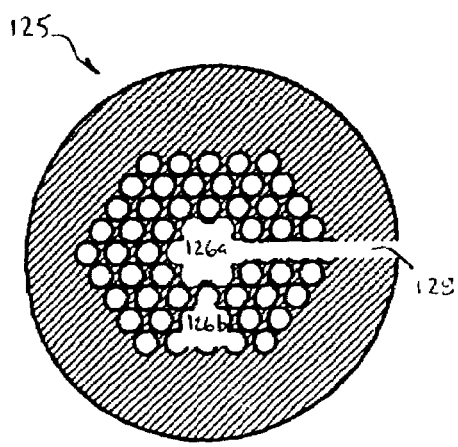
Figure 8F:
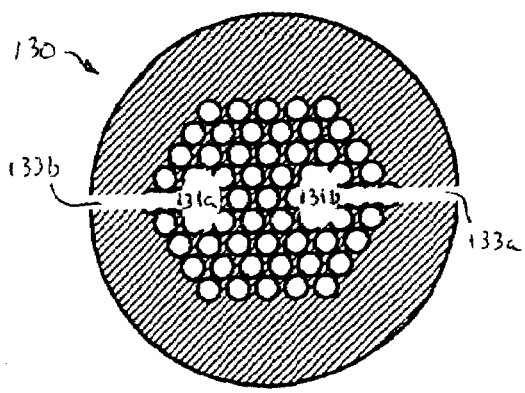

FIGS. 8A and 8B illustrate preforms 106, 110 which may advantageously be used to manufacture fiber sensors of the invention having the same cross sectional shape. In the preform of FIG. 8A an extra, tubular cladding layer 108 is provided around a preform of a fiber sensor 3, and is fused into the cladding of the fiber 3 opposite from slot 13. During drawing of the fiber from the preform 106, the pressure of the gas within the hollow area 107 is maintained at a selected level so that the slot 13 of the preform 106 does not collapse. In this way the slot 13 is maintained in the resulting fiber without the need for laser machining or chemical etching. In the final-fiber, a slot (not shown) or other opening may be cut in the extra, tubular cladding 108 to expose the fiber slot 13 to the ambient atmosphere. In the preform of FIG. 8B, the extra, tubular cladding layer 112 is fused on the sides of the fiber preform 45 opposite the double sided slots 28a, 28b. During the drawing of the fiber from the preform 110, the pressure of the gas within the hollow spaces 113a, 113b is maintained at a selected level so that the slots 28a, 28b do not collapse. After the drawing step is completed, a slot or other opening 114 is cut into the side of the extra, tubular cladding layer 112 to admit the ambient atmosphere to the slots 28a, 28b and into the hollow core 5 of the fiber. Again, an advantage of this design is that the need for laser machining or etching of the slots 28a, 28b is obviated. While both embodiments 106, 110 require the cutting or etching of a slot or other opening in the outer cladding 108, 112, such a slot or opening does not have to penetrate into the hollow core and hence may be made relatively easily when compared with the difficulty of fabricating a slot that penetrates a hollow core 5 through a microstructure cladding 7. Additionally, in the absence of an opening in the outer cladding, such a design will have faster time response because the larger volume contained in void 107 or voids 113a and 113b will increase the axial fluid flow through the fiber.

FIGS. 8C-8F illustrate embodiments 116, 120, 125 and 130 of the fiber sensor having dual hollow cores 117a, 117b; 121a, 121b; 126a, 126b and 131a, 131b. Having two or more hollow cores can provide a number of potentially useful optical effects by providing the elements of two or more different ridge type optical waveguides that conduct different modes which may be compared. For example, a comparison of the relative intensity of the modes conducted through the cores 117a, 117b and 121a, 121b may be used to determine a flow direction of a target gas or other fluid flowing through the sides of the fiber sensor 116, 120. In the embodiment 125 of FIG. 8E, the relative intensity of the modes exposed to and insulated from the ambient environment in cores 126a, 126b, respectively, may be compared. Hence measurements of the mode intensity through the core 126b may act as a baseline for the core 126a which is exposed to the ambient environment via slot 128. In the embodiment 130 of FIG. 8F, the relative intensity of the modes exposed to different sides of the ambient environment in cores 131a, 131b, respectively, may be compared, as slots 133a, 133b expose their respective cores to the environment on opposite sides of the fiber sensor.

Figure 9A:
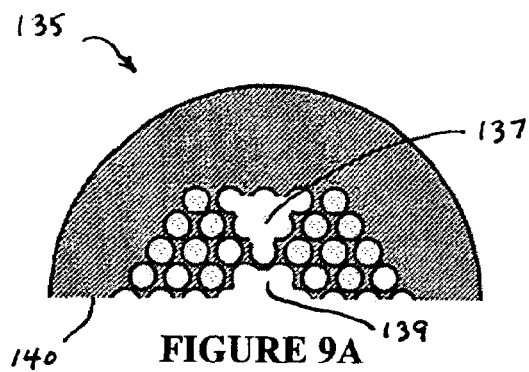
FIGS. 9A-9C are side, cross-sectional views of different embodiments of the fiber sensor having one or two off-center hollow cores, wherein the elongated side opening takes the form of a flat-sided section of cladding to expose one or more of the hollow cores to the ambient environment such that the resulting fiber has a "D" shaped cross-section.
Figure 9B:
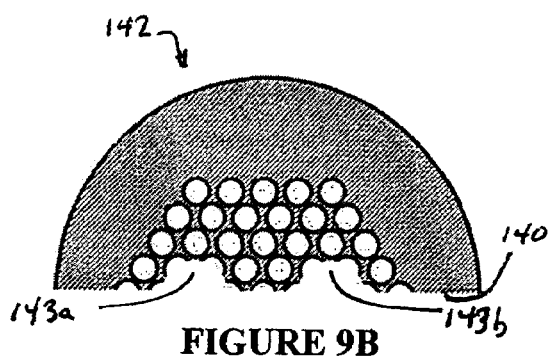
Figure 9C:
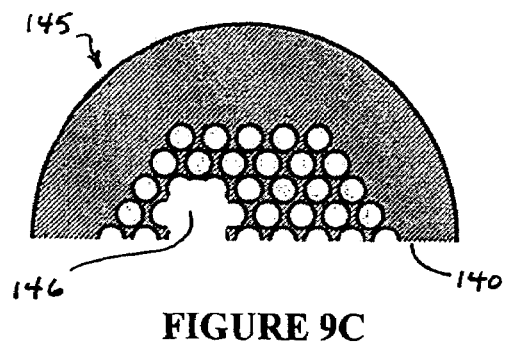

FIGS. 9A-9C illustrate embodiments 135, 142 and 145 of the fiber sensor wherein a flat sided section of the fiber has been removed to expose one or more hollow cores 137,139; 143a, 143b, and 146 to the ambient environment, giving each of these fibers a "D" shaped cross section. The provision of an unexposed core 137 in the embodiment 135 provides the opportunity for establishing a comparative baseline with the mode conducted through the exposed hollow core 139 in the same manner as described with respect to FIG. 8E. The provision of two exposed cores 143a, 143b in the FIG. 9B embodiment may be used in the manner described with respect to the FIG. 8C embodiment. While all the embodiments 135, 142 and 145 have the advantage of a near-instantaneous response time, the infinitely wide slot provided by the removal of a flat sided section of the outer wall of these fiber sensors unfortunately reduces the amount of coupling the fiber exerts on the mode and hence exacerbates signal loss. However, much of this signal loss can be compensated for by coiling such fiber sensors 135, 142 and 145 in the manner indicated in FIG. 10, with the flat side 155a of the D shaped cross section facing the interior of the coil or spiral 157, and the rounded side 155b facing the outside of the coil or spiral 157. Such bending more tightly confines the optical mode to the ridge of the waveguide defined by the hollow core by biasing the path of the light more toward the hollow core and less toward the flat side that defines the slab of the waveguide. However, for such bending to be effective, the bend radius must be below a certain value to significantly improve the confinement of the optical mode.

Figure 11A:
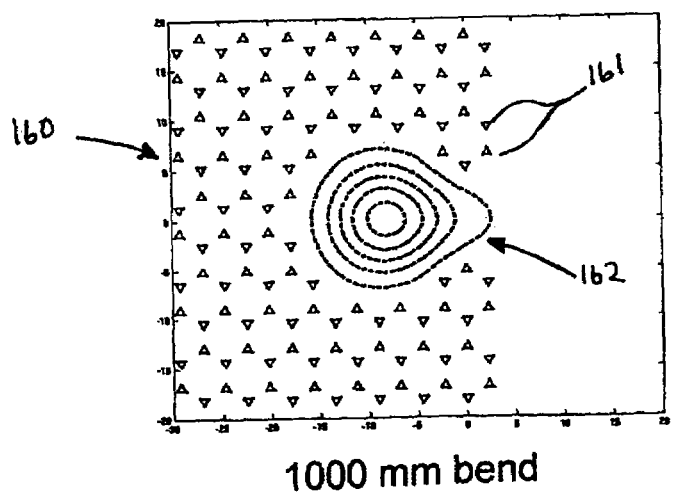
FIGS. 11A-11C are intensity profiles, illustrated by optical contours at 10%, 30%, 50%, 70% and 90% of a fundamental mode of the structure similar to that illustrated in FIG. 10 for bend radii of 1000 mm, 10 mm and 5 mm respectively, illustrating generally how mode confinement improves with a reduction in bend radius.
Figure 11B:
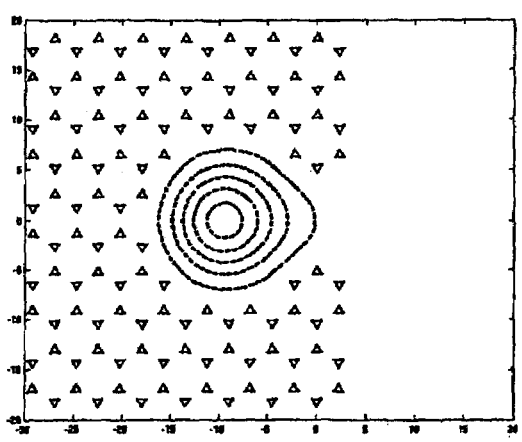
Figure 11C:
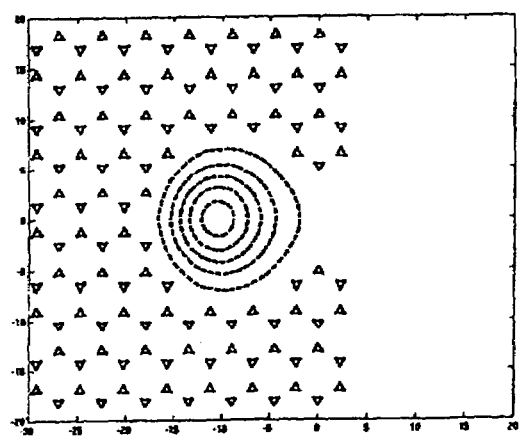

FIGS. 11A-11C are computer simulations optical contours at 10%, 30%, 50%, 70% and 90% of the intensity profiles of a fundamental mode at bending radii of 1000 mm, 10 mm and 5 mm, respectively, illustrating generally how mode confinement improves with a reduction in bend radius. Although the structure 160 in FIGS. 11A-11C is made up of disconnected triangular elements 161, such structures are excellent approximations to real structures with very high air-filling fraction. These simulations indicate that a substantial amount of losses may be compensated for by coiling such D profile fibers with a bend radius of at least about 10 mm, and more preferably with a bend radius of 5 mm. Of course the bend radius is constrained by the diameter of the fiber sensor, as larger diameter fibers are apt to break when bent beneath a certain critical radius. Accordingly, fiber diameters between 50-150 microns are generally preferred, and fiber diameters of between about 70-80 microns are most preferred. The selection of this range of diameter radii is the result of the following analysis:

Minimum mechanical bend radius—the threshold bend radius for which the bend-induced stresses will lead to failure in a time shorter than the acceptable lifetime of the fiber in a given application. When a fiber is bent, the outside of the bend is under tensile stress and the inside under compressive stress. The bending stress can be calculated as:

$$\sigma \text{bending} = E(r_f/R)$$

where:
  E=Young's modulus=10440 kpsi (72 GPa)
  $r_f$=Fiber radius
  R=Bend radius Under such stress, the time to failure can then be approximately calculated using a simple power law model:

$$T_f = (\sigma_p/\sigma_a)^m$$

where:
  $T_f$=Time to failure (seconds)
  $\sigma_p$=Prooftest stress
  $\sigma_a$=Application stress=bending stress or a bending
  m=Fatigue factor (typically 20 for standard fibers)

In the fibers embodied in this application we anticipate that m will be significantly reduced because of the complex surface geometry. One way to improve the time to failure is to reduce the fiber radius $r_f$ thereby reducing the bending stress.

The structure 160 used in FIGS. 11A-11C is an example of a multimode core 162. For some applications (including interferometric detection) it may be advantageous to have single-mode propagation in the hollow core of the ridge waveguide. However, in order to achieve fast response times and high sensitivity it may be advantageous to have a large core (as shown in FIG. 11A) that supports many optical modes.

Figure 12A:
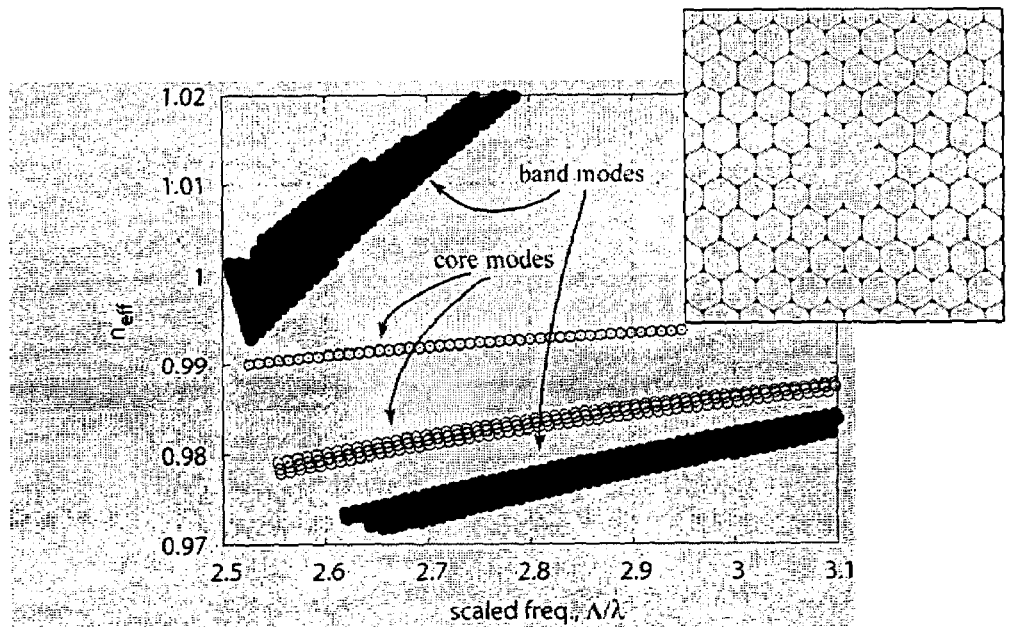
FIGS. 12A and 12B are band-gap diagrams comparing the optical modes of a photonic band gap fiber sensor having no elongated side opening and hence no air slab vs. a photonic band gap fiber sensor embodying the invention.
Figure 12B:
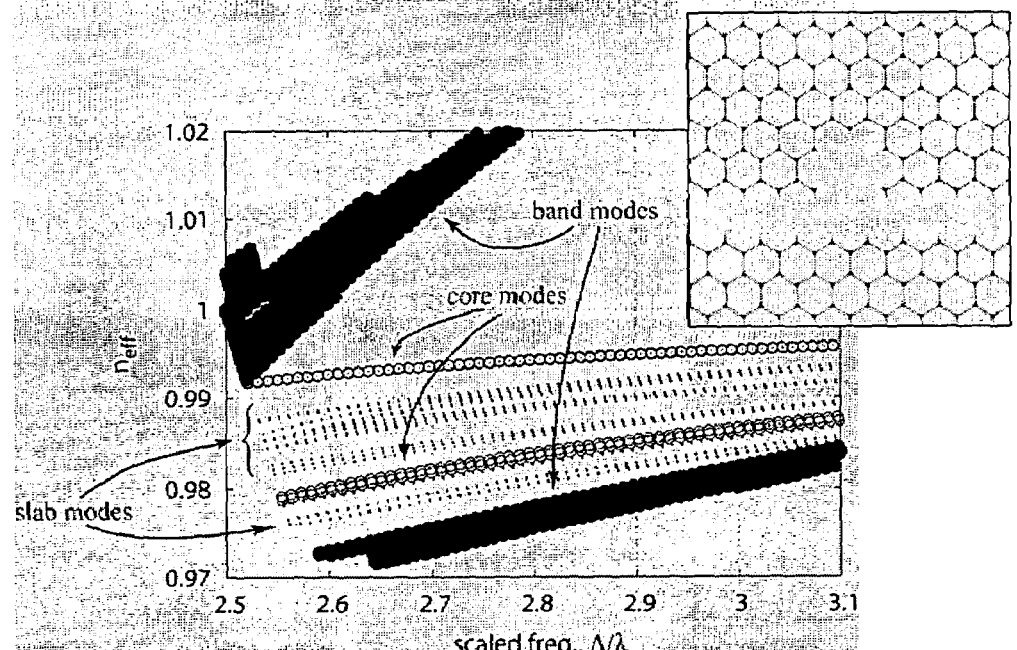

FIGS. 12A and 12B illustrate the optical modes of fiber sensors of the invention vs. the modes of conventional photonic band gap fibers. As indicated previously, the slot or slots in the side wall of a photonic band gap fiber provides the slab of a ridge type photonic waveguide. This air slab in turn introduces many new slab modes into the band gap as compared to the modes associated with a conventional photonic band gap fiber, as can be seen by a comparison of FIGS. 12A and 12B. However, the graph of FIG. 12B also shows that these modes do not cross the core-guided modes, which in turn indicates that coupling between the new modes and the core guided modes will be minimal, and will not significantly act to attenuate or distort any signal generated by fiber sensors of the invention.

Figure 13A:
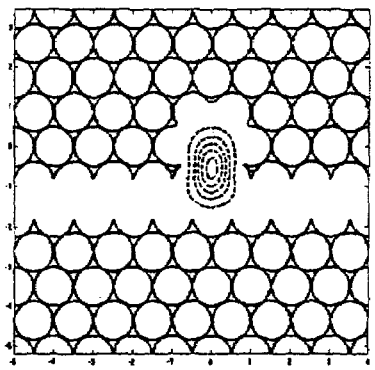
FIGS. 13A-13F illustrate different guided modes of a same embodiment as FIG. 12B of the invention.
Figure 13B:
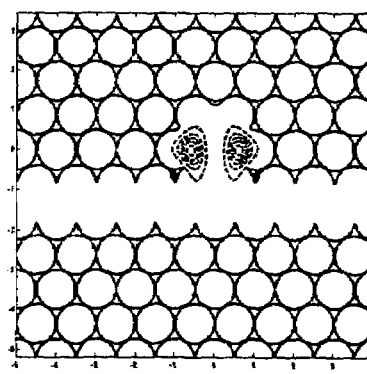
Figure 13C:
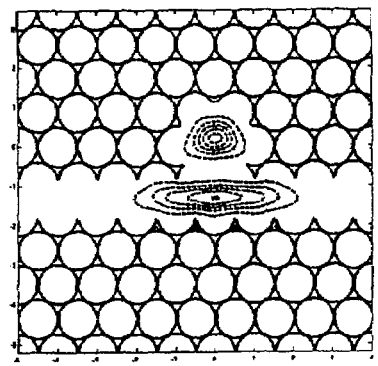
Figure 13D:
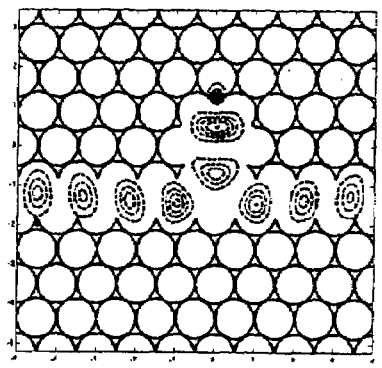
Figure 13E:
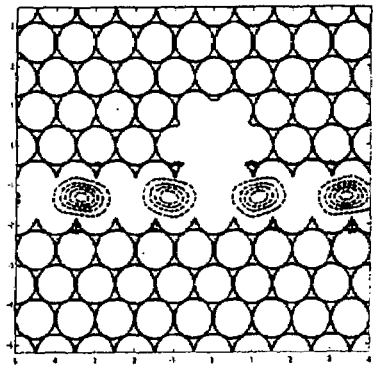
Figure 13F:
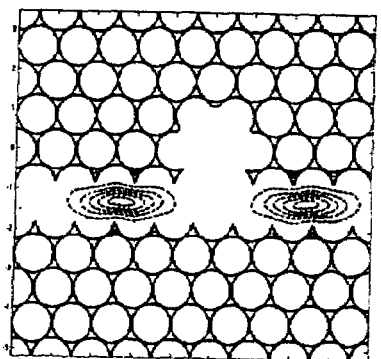

Finally, FIGS. 13A-13F illustrates different guided modes of a same embodiment of the invention. FIGS. 13A and 13B illustrate modes that are guided in the core only, while FIGS. 13C and 13D illustrate modes that are guided in both the core and the slab. FIGS. 13E and 13F illustrate modes that are guided exclusively in the slab.

In addition to the optical modes shown in FIGS. 13A-13F there are additional optical modes that exist along the inner surface boundaries of the structure. These additional modes are referred to as surface modes and they only exist when the appropriate surface termination is chosen. In FIG. 13A it can be seen that the core can be formed by cutting a perfect circle of material out of the periodic lattice. Because of the existing air holes that define the structure, this removal of material leaves behind a fluted shape. Likewise the slab can be formed by cutting a rectangular slot out of the periodic lattice leaving behind a fluted air channel. The relative positions of the aforementioned circle and rectangle with respect to the lattice periodicity define the surface terminations in the core and slab regions. The surface termination may be different in these regions so that surface modes may only exist in part of the ridge waveguide. The surface modes have an enhanced interaction with the surface of the structure and thus it may be advantageous to coat the ridge waveguide surface with material to detect the presence of target species through chemical binding, for example.

The embodiments in FIGS. 1-13 can be fabricated using a fiber-draw processes, extrusion processes, direct machining (such as drilling or milling) or planar-processing techniques as found in semiconductor device fabrication. The design of the sensor 3 may be modified to accommodate the processing requirements while maintaining the advantages of the invention. In planar geometries the device may be fabricated at the final intended scale. In fiber geometries the structure can be fabricated in a macroscopic preform that can be reduced in size to attain the desired scale to achieve the properties required for the invention.

While this invention has been described with respect to a number of specific examples, many variations, modifications and additions to this invention will become apparent to persons of skill in the art. All such variations, modifications and additions are intended to be encompassed within the invention, which is limited only by the appended claims and equivalents thereto.

We claim:

1. An optical waveguide environmental sensor, comprising:
  a cladding at least partially surrounding a hollow core portion that extends along or parallel to a longitudinal, center axis of said cladding and defines a light transmission path through said waveguide, and
  at least one elongated side opening in said cladding that extends parallel to said longitudinal center axis and exposes said hollow core portion to the ambient environment, wherein the hollow core portion and elongated opening jointly support at least one bound optical mode.

2. The optical waveguide environmental sensor defined in claim 1, wherein said hollow core portion, said elongated opening, and said cladding form an optical ridge waveguide.

3. The optical waveguide environmental sensor defined in claim 1, wherein said cladding includes a photonic band gap structure that partially surrounds said hollow core portion.

4. The optical waveguide environmental sensor defined in claim 3, wherein said cladding includes a microstructured material having a periodic variation in an index of refraction.

5. The optical waveguide environmental sensor defined in claim 3, wherein said cladding includes a Bragg reflector including alternating layers of material having different indexes of refraction that partially surrounds said hollow core portion.

6. The optical waveguide environmental sensor defined in claim 1, wherein said cladding includes a plurality of elongated openings, each of which penetrates the cladding in a direction transverse to said longitudinal axis and exposes said hollow core portion to the ambient environment.

7. The optical waveguide environmental sensor defined in claim 1, wherein said plurality of elongated openings are symmetrically disposed around said cladding to eliminate birefringence.

8. The optical waveguide environmental sensor defined in claim 1, wherein said elongated opening is a slot-like groove that extends only through one side of said cladding to said hollow core portion.

9. The optical waveguide environmental sensor defined in claim 1, wherein said elongated opening is a slot-like groove that extends through both sides of said cladding and through said hollow core portion.

10. The optical waveguide environmental sensor defined in claim 3, wherein said hollow core portion is disposed in the center of said photonic band-gap structure when said waveguide is viewed in transverse cross-section.

11. The optical waveguide environmental sensor defined in claim 3, wherein said hollow core portion is disposed off-center in said photonic band-gap structure when said waveguide is viewed in transverse cross-section.

12. The optical waveguide environmental sensor defined in claim 3, wherein said photonic bandgap structure is centered with respect to said cladding when said waveguide is viewed in transverse cross-section.

13. The optical waveguide environmental sensor defined in claim 3, wherein said photonic band gap structure is disposed off-center with respect to the cladding when the waveguide is viewed in transverse cross-section.

14. The optical waveguide environmental sensor defined in claim 1, wherein a transverse axis of said elongated opening is aligned with a center of said hollow core portion.

15. The optical waveguide environmental sensor defined in claim 1, wherein a transverse axis of said elongated opening is aligned off-center with respect to said hollow core portion.

16. The optical waveguide environmental sensor defined in claim 1, wherein said elongated opening is defined by a removed, wedge-shaped section of cladding such that side walls of the elongated opening are disposed at an angle to one another when the waveguide is viewed in a transverse cross-section.

17. The optical waveguide environmental sensor defined in claim 1, wherein said elongated opening is defined by a removed, flat-sided section of cladding such that side walls of the elongated opening are co-planar when the waveguide is viewed in a transverse cross-section.

18. The optical waveguide environmental sensor defined in claim 17, wherein said optical waveguide is bent around a radius with the elongated opening on the inside and the cladding on the outside such that optical losses are substantially reduced.

19. The optical waveguide environmental sensor defined in claim 17, wherein said optical waveguide is bent around a radius in a spiral configuration.

20. The optical waveguide environmental sensor defined in claim 1, wherein said cladding includes a plurality of hollow core portions which are optically coupled to one another and wherein said elongated opening in said cladding exposes at least one of said hollow core portions to the ambient environment.

21. The optical waveguide environmental sensor defined in claim 20, wherein said cladding includes a plurality of elongated openings, each of which penetrates said cladding in a direction transverse to said longitudinal axis and exposes a different one of said hollow core portions to the ambient environment.

22. The optical waveguide environmental sensor defined in claim 1, wherein the elongated opening extends substantially the length of the waveguide.

23. An optical fiber environmental sensor, comprising:
a cladding having an exterior surface, and a photonic band gap structure in its interior that partially surrounding a hollow core portion that extends along or parallel to a longitudinal, center axis of said cladding and defines a light transmission path through said fiber, and
at least one elongated side opening in said cladding that extends parallel to said longitudinal center axis and penetrates said cladding in a direction transverse to said longitudinal axis and exposes said hollow core portion to the ambient environment,
wherein the hollow core portion and elongated opening jointly support at least one bound optical mode.

24. The optical fiber environmental sensor defined in claim 23, wherein an ambient gas or liquid contained within the hollow core portion and the elongated opening form a ridge and slab, respectively, of an optical ridge waveguide that conducts said at least one bound optical mode.

25. The optical fiber environmental sensor defined in claim 23, wherein the photonic band gap structure includes a microstructured material having a periodic variation in an index of refraction.

26. The optical fiber environmental sensor defined in claim 23, wherein the photonic band gap structure is a Bragg reflector including alternating layers of material having different indexes of refraction that at least partially surround said hollow core portion.

27. The optical fiber environmental sensor defined in claim 23, wherein said cladding includes a plurality of elongated openings, each of which penetrates the cladding in a direction transverse to said longitudinal axis and exposes said hollow core portion to the ambient environment.

28. The optical fiber environmental sensor defined in claim 27, wherein said plurality of elongated openings are symmetrically disposed around said cladding to eliminate birefringence.

29. The optical fiber environmental sensor defined in claim 23, wherein said elongated opening is defined by a removed, wedge-shaped section of cladding such that side walls of the elongated opening are disposed at an angle to one another when the fiber is viewed in transverse cross-section.

30. The optical fiber environmental sensor defined in claim 23, wherein said elongated opening is defined by a removed, flat-sided section of cladding such that side walls of the elongated opening are co-planar when the fiber is viewed in transverse cross-section.

31. The optical fiber environmental sensor defined in claim 30, wherein said optical fiber is bent around a radius with the elongated opening on the inside and the cladding on the outside such that photonic losses are substantially reduced.

32. The optical fiber environmental sensor defined in claim 31, wherein said optical waveguide is bent around a radius of less than 10 mm in a spiral configuration.

33. The optical fiber environmental sensor defined in claim 31, wherein said optical waveguide is bent around a radius of less than 5 mm in a spiral configuration.

34. The optical fiber environmental sensor defined in claim 23, wherein the cladding has a substantially cylindrical outer surface.

35. The optical fiber environmental sensor defined in claim 25, wherein said microstructure includes a pattern of holes in a light conducting material, and wherein a width of the hollow core portion when viewed in transverse cross section is substantially larger than a pitch between the pattern of holes.

36. A method of fabricating an optical waveguide environmental sensor, comprising the steps of:
forming an elongated optical waveguide from a light conducting material that contains a hollow core portion surrounded by photonic band gap structure, and
forming an elongated opening in a side of said waveguide that is parallel to a longitudinal axis of said waveguide that exposes said hollow core portion to the ambient environment.

37. The method of fabricating an optical waveguide environmental sensor defined in claim 36, wherein said step of forming said elongated optical waveguide includes the drawing of an air-core photonic band-gap fiber from a light conducting material.

38. The method of fabricating an optical waveguide environmental sensor defined in claim 37, wherein said step of forming said elongated opening includes a step of chemically etching said opening in a side wall of said fiber.

39. The method of fabricating an optical waveguide environmental sensor defined in claim 38, wherein said step of forming said elongated opening includes a step of providing a section of material in a side of said optical fiber having a higher etch rate to facilitate the step of chemically etching said opening in a side wall of said fiber.

40. The method of fabricating an optical waveguide environmental sensor defined in claim 37, wherein said step of forming said elongated opening includes a step of laser machining said opening in a side wall of said optical fiber.

41. The optical waveguide environmental sensor defined in claim 1, wherein said cladding includes a plurality of hollow core portions which are not optically coupled to one another and wherein said elongated opening in said cladding exposes at least one of said hollow core portions to the ambient environment.

42. The environmental sensor of claim 1 further including a light source and a photodetector.

43. The optical waveguide environmental sensor defined in claim 1, wherein said elongated opening is defined by a removed, flat-sided section of cladding.

* * * * *